(12) United States Patent
Deng et al.

(10) Patent No.: US 10,718,749 B2
(45) Date of Patent: Jul. 21, 2020

(54) METHODS FOR QUANTIFYING NITROGEN-CONTAINING COMPOUNDS IN SUBTERRANEAN TREATMENT FLUIDS

(71) Applicant: Halliburton Energy Services, Inc., Houston, TX (US)

(72) Inventors: Zhao Deng, Kingwood, TX (US); Jay Paul Deville, Spring, TX (US); Philip Wayne Livanec, Houston, TX (US)

(73) Assignee: Hallibunon Energy Services, Inc., Houston, TX (US)

( * ) Notice: Subject to any disclaimer, the term of this patent is extended or adjusted under 35 U.S.C. 154(b) by 70 days.

(21) Appl. No.: 15/560,154

(22) PCT Filed: Apr. 20, 2015

(86) PCT No.: PCT/US2015/026675
§ 371 (c)(1),
(2) Date: Sep. 20, 2017

(87) PCT Pub. No.: WO2016/171655
PCT Pub. Date: Oct. 27, 2016

(65) Prior Publication Data
US 2018/0080917 A1 Mar. 22, 2018

(51) Int. Cl.
*G01N 33/88* (2006.01)
*G01N 33/00* (2006.01)
(Continued)

(52) U.S. Cl.
CPC ............ *G01N 33/442* (2013.01); *C01C 1/28* (2013.01); *G01N 1/4022* (2013.01); *G01N 30/88* (2013.01);
(Continued)

(58) Field of Classification Search
CPC .... G01N 33/442; G01N 1/4022; G01N 30/88; G01N 33/00; G01N 15/06; G01N 33/48; G01N 35/00
(Continued)

(56) References Cited

U.S. PATENT DOCUMENTS 2,855,365 A 10/1958 Burleson
3,363,990 A * 1/1968 Blom .................. B67C 3/12
422/75
(Continued)

OTHER PUBLICATIONS

"A Guide to Kjeldahl Nitrogen Determination Methods and Apparatus," Labconco, undated, 13 pages.
(Continued)

*Primary Examiner* — Brian J. Sines
(74) *Attorney, Agent, or Firm* — Tenley Krueger; C. Tumey Law Group PLLC (57) ABSTRACT

It can sometimes be difficult to quantify the amount of polymer present in a subterranean treatment fluid, particularly at a job site. Methods for analyzing a treatment fluid for a polymer can comprise: receiving a sample of a treatment fluid comprising a nitrogen-containing polymer; placing the sample of the treatment fluid and an aqueous base in an oilfield retort; heating the sample of the treatment fluid and the aqueous base together in the oilfield retort at least until the nitrogen-containing polymer has been substantially hydrolyzed to one or more volatile nitrogen compounds; distilling the one or more volatile nitrogen compounds from the oilfield retort; and determining a quantity of the nitrogen-containing polymer in the sample of the treatment fluid based upon a quantity of the one or more volatile nitrogen compounds distilled from the oilfield retort. Analyses of other nitrogen-containing compounds may take place similarly.

13 Claims, 2 Drawing Sheets

(51) Int. Cl.
*G01N 15/06* (2006.01)
*G01N 33/48* (2006.01)
*G01N 35/00* (2006.01)
*G01N 33/44* (2006.01)
*C01C 1/28* (2006.01)
*G01N 1/40* (2006.01)
*G01N 30/88* (2006.01)
*E21B 41/00* (2006.01)

(52) U.S. Cl.
CPC ...... *E21B 41/00* (2013.01); *G01N 2001/4033* (2013.01)

(58) Field of Classification Search
USPC .............. 436/106, 113, 114; 422/68.1
See application file for complete search history.

(56) References Cited

U.S. PATENT DOCUMENTS

| | | | |
|---|---|---|---|
| 3,429,909 A * | 2/1969 | Schuster | C07F 5/022 |
| | | | 558/289 |
| 3,905,770 A * | 9/1975 | Mossberg | G01N 31/002 |
| | | | 222/442 |
| 4,081,345 A | 3/1978 | Tolg et al. | |
| 4,223,726 A * | 9/1980 | Cha | E21B 43/247 |
| | | | 166/250.15 |
| 4,229,180 A * | 10/1980 | Christoffersen | B01J 23/18 |
| | | | 436/114 |
| 5,306,909 A | 4/1994 | Jones et al. | |
| 5,557,103 A | 9/1996 | Hughes et al. | |
| 5,968,835 A * | 10/1999 | Aoki | G01N 31/005 |
| | | | 436/110 |
| 6,287,868 B1 | 9/2001 | Persson | |
| 2006/0011547 A1 * | 1/2006 | Bell | B01D 15/34 |
| | | | 210/656 |
| 2006/0137878 A1 | 6/2006 | Haberman | |
| 2010/0216672 A1 | 8/2010 | Todd | |
| 2013/0277113 A1 * | 10/2013 | Murphy | G01N 1/4022 |
| | | | 175/46 |
| 2014/0116778 A1 | 5/2014 | Deville et al. | |
| 2018/0080917 A1 * | 3/2018 | Deng | C01C 1/28 |

OTHER PUBLICATIONS

"PHPA Polymer Concentration Test Kit," Fann Instrument Company, 2007, 1 page.
McCulley et al., "A New Method for the Quantitative Determination of the PHPA Polymer Content of Drilling Fluids and Other Aqueous Systems," Oct. 1991, SPE Annual Technical Conference and Exhibition, SPE-22580-MS, 2 pages (Abstract Only).
International Search Report and Written Opinion from PCT/US2015/026675, dated Nov. 25, 2015, 16 pages.

* cited by examiner

METHODS FOR QUANTIFYING NITROGEN-CONTAINING COMPOUNDS IN SUBTERRANEAN TREATMENT FLUIDS

BACKGROUND

The present disclosure generally relates to subterranean treatment fluids and, more specifically, to methods for quantifying nitrogen-containing polymers and other nitrogen-containing compounds in treatment fluids.

Treatment fluids may be used in a variety of subterranean treatment operations. Such treatment operations can include, without limitation, drilling operations, stimulation operations, production operations, remediation operations, sand control treatments, and the like. As used herein, the terms "treat," "treatment," "treating," and grammatical equivalents thereof refer to any subterranean operation that uses a fluid in conjunction with achieving a desired function and/or for a desired purpose. Use of these terms does not imply any particular action by the treatment fluid or a component thereof, unless otherwise specified herein. More specific examples of illustrative treatment fluids can include, for example, drilling fluids, fracturing fluids, gravel packing fluids, acidizing fluids, conformance fluids, scale dissolution and removal fluids, diverting fluids, and the like.

A drilling fluid or drilling mud is a designed fluid intended for circulation through a wellbore to facilitate a drilling operation. Functions of a drilling fluid can include, without limitation, removing drill cuttings from the wellbore, cooling and lubricating the drill bit, aiding in the support of the drill pipe and the drill bit, and forming a hydrostatic head to maintain integrity of the wellbore walls and/or to prevent blowouts from occurring. Drilling fluids may be water-based or oil-based and may sometimes be in the form of an emulsion.

One or more polymers may be included in a drilling fluid in order to facilitate the above-described drilling fluid functions. The included polymer(s) can be soluble or insoluble (e.g., suspended or emulsified) in the continuous phase of the drilling fluid. When the continuous phase of the drilling fluid is water-based, for instance, acrylamide polymers and copolymers are commonly used. Although acrylamide polymers and copolymers represent one class of polymers that may be used in drilling fluids, other types of nitrogen-containing polymers, possibly having different solubility properties, may be present instead. For example, polyamides and nitrile-containing polymers may be insoluble in the continuous phase of a water-based drilling fluid.

Polymers may be used in other types of treatment fluids as well. Illustrative functions of polymers, particularly nitrogen-containing polymers, in other types of treatment fluids include, for example, viscosification, conformance control, permeability modification or relative permeability modification, friction control, scale inhibition, and the like.

Because they may markedly impact the properties and functionality of drilling fluids and other types of treatment fluids, it is often desirable to know with some certainty the quantity of a polymer additive that is present in a drilling fluid or other type of treatment fluid sample at a given point in time. However, polymer assays can be non-straightforward and time-consuming depending on the sample characteristics and the particular type of polymer that is present. In many instances, highly specialized and labor-intensive analyses may be needed for certain types of polymers and/or to accommodate the particular characteristics of a given fluid sample.

Because acrylamide polymers and copolymers enjoy widespread use in the oilfield, a number of wet-chemical analyses have been developed for these types of polymers. Illustrative techniques for assaying water-soluble acrylamide polymers and copolymers include precipitating a tin complex of the polymer and weighing the tin complex following centrifugation, or conducting a hydrolysis of the polymer under mild alkaline conditions. These analyses are not considered to be amenable to polymers in insoluble form, nor are they considered to be broadly applicable to other types of polymers that may be present in treatment fluids. The analyses commonly used for acrylamide polymers and copolymers also require equipment and skills that are not routinely present at a job site. Furthermore, considerable processing time and labor may be involved in conventional polymer analyses, potentially providing untimely and economically unfavorable support of an ongoing treatment operation.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

The present disclosure generally relates to subterranean treatment fluids and, more specifically, to methods for quantifying nitrogen-containing polymers and other nitrogen-containing compounds in treatment fluids.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, wet-chemical polymer analyses may be highly geared toward a particular polymer and type of sample undergoing analysis. Generally, these analyses are not extendable to a larger class of polymers, including those that may be present in insoluble form, and they may be difficult to perform at a job site. These deficiencies can make it difficult to determine the quantity of a polymer in a treatment fluid with sufficient rapidity and precision to enable some degree of regulation over an ongoing subterranean treatment operation.

As further discussed above, nitrogen-containing polymers are widely used in drilling fluids and other types of treatment fluids. Acrylamide polymers and copolymers, for example, are frequently employed due to their ready solubility in aqueous fluids. The present inventors discovered that nitrogen-containing polymers and other types of nitrogen-containing compounds may be readily analyzed by modifying the use of existing equipment commonly found at an oilfield job site. Advantageously, the methods discovered by the inventors are amenable for analyzing nitrogen-containing polymers and other nitrogen-containing compounds present in either soluble or insoluble form in a treatment fluid sample. Moreover, the present methods are relatively insensitive to the nature of the sample's fluid phase and other components present therein in combination with the polymer, as discussed hereinbelow.

More specifically, the inventors discovered that analyses of nitrogen-containing polymers and other types of nitrogen-containing compounds in treatment fluids can be facilitated through use of an oilfield retort. Conventional oilfield retorts are distillation systems comprising a heater, a sample cell in thermal communication with the heater, and a condensation column in fluid communication with the sample cell. Oilfield retorts are commonly found at an oilfield job site and are typically used for determining the oil-water ratio (OWR) and solids content of various oilfield fluids by distilling a sample at high temperatures and subsequently measuring the amount of volatile material and non-distillable solids. The volatile material is collected in a graduated receiving vessel after being re-liquefied in the condensation column. When operated in this manner, oilfield retorts are conventionally operated at elevated temperatures, often in the 900-1000° F. range.

Figure 1:
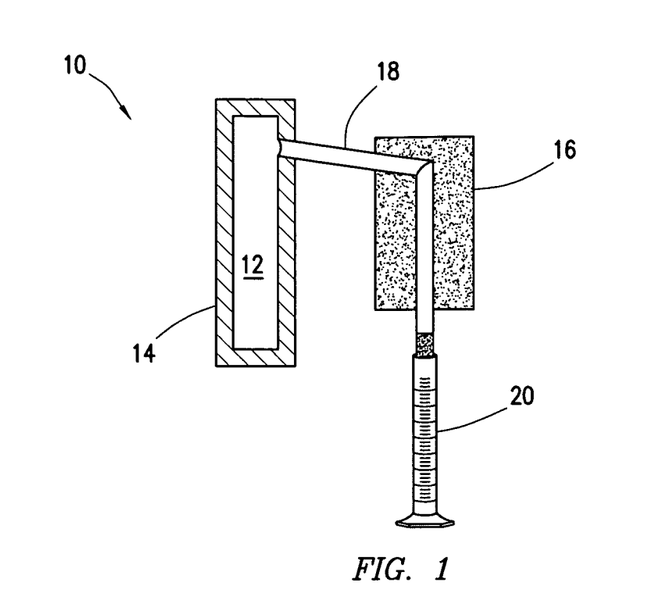
FIG. 1 shows an illustrative schematic of an oilfield retort conventionally coupled to a graduated receiving vessel.

FIG. 1 shows an illustrative schematic of an oilfield retort conventionally coupled to a graduated receiving vessel. As shown in FIG. 1, oilfield retort 10 contains heating jacket 14 substantially surrounding retort cell 12. Distillate from retort cell 12 is received via line 18 in condensation column 16. After the volatile material in the distillate liquefies in condensation column 16, the liquid is collected in graduated receiving vessel 20 and the volume is determined.

In contrast to the conventional use modality of oilfield retorts, in which the retorts are used simply to distill a sample, the present inventors discovered that retorts may also be used to promote a chemical reaction in conjunction with a modified Kjeldahl-type nitrogen analysis. In particular, the inventors discovered that oilfield retorts may be used to promote a degradation reaction of nitrogen-containing polymers and other types of non-volatile nitrogen containing compounds to form volatile nitrogen compounds that may be distilled from the retort cell and collected from the output of the retort's condensation column. In some embodiments, the degradation reaction may comprise a hydrolysis reaction. The collected volatile nitrogen compounds can then be quantitatively assayed in an appropriate manner, and the result can be correlated to the quantity of nitrogen-containing polymers or other nitrogen-containing compounds that were originally present.

Use of oilfield retorts in the foregoing manner to promote a degradation reaction may provide a number of advantages over conventional field analyses of nitrogen-containing polymers and other nitrogen-containing compounds in treatment fluids. Foremost, oilfield retorts are commonly present at an oilfield job site and are readily compatible with the harsh conditions that are associated therewith. As such, oilfield retorts provide a more rugged system for promoting Kjeldahl-type nitrogen analyses than do more fragile systems, such as laboratory glassware, that are relatively incompatible with job site conditions. In addition, oilfield retorts are capable of providing high temperatures and rapid heating rates that may promote hydrolysis of nitrogen-containing polymers and other nitrogen-containing compounds to form volatile nitrogen compounds in a short amount of time. The rapid heating rates and high temperatures allow complete or near-complete degradation (e.g., through a hydrolysis reaction) to take place in a short amount of time in order to provide relatively rapid analytical feedback.

Although oilfield retorts may provide operating temperatures nearing 1000° F., the inventors surprisingly discovered that more efficient hydrolyses and better analytical precision may be realized at lower temperatures, such as in a range from about 500° F. to about 700° F. Accordingly, the inventors identified that it can be desirable to regulate the thermal output of the oilfield retort during the production of volatile nitrogen compounds. Without being bound by theory or mechanism, the inventors believe that conducting a hydrolysis reaction at higher temperatures may result in inefficient collection of the volatile nitrogen compounds at the output of the oilfield retort's condensing column and/or decomposition of the nitrogen-containing polymer or nitrogen-containing compound into a non-hydrolyzable char or tar within the retort cell. Similarly, conducting a hydrolysis reaction at lower temperatures may result in a reaction that is either incomplete or overly slow, thereby providing untimely or inaccurate results.

In addition, the inventors discovered that by partially blocking the upper portions of the retort cell with a non-reactive and porous material, such as steel wool or glass wool, for example, more accurate analyses can be attained. Remaining unbound by theory or mechanism, it is believed that the non-reactive and porous material effectively turns the partially blocked portion of the retort cell into a fractional distillation column and increases its number of theoretical plates. By increasing the number of theoretical plates, the partially blocked retort cell can result in more vigorous reflux of the reaction mixture within the retort cell, thereby promoting more complete formation of volatile nitrogen compounds for subsequent quantification.

In various embodiments, methods described herein may comprise: receiving a sample of a treatment fluid comprising a nitrogen-containing compound; placing the sample of the treatment fluid and an aqueous base in an oilfield retort; heating the sample of the treatment fluid and the aqueous base together in the oilfield retort at least until the nitrogen-containing compound has been substantially degraded to one or more volatile nitrogen compounds; distilling the one or more volatile nitrogen compounds from the oilfield retort; and determining a quantity of the nitrogen-containing compound in the sample of the treatment fluid based upon a quantity of the one or more volatile nitrogen compounds distilled from the oilfield retort.

In some embodiments, the nitrogen-containing compound may comprise a nitrogen-containing polymer. Illustrative examples of nitrogen-containing polymers that may be analyzed by the methods of the present disclosure are discussed hereinbelow. Although some embodiments herein are described with reference to a nitrogen-containing polymer, it is to be recognized that a non-polymeric nitrogen-containing compound may be substituted for analysis in a substantially similar manner. In general, any nitrogen-containing polymer or nitrogen-containing compound that may be degraded to form one or more volatile nitrogen compounds may be analyzed by the methods described herein. In more particular embodiments, suitable nitrogen-containing polymers and nitrogen-containing compounds may be degradable by a hydrolysis reaction to form the one or more volatile nitrogen compounds.

In more specific embodiments, nitrogen-containing polymers and nitrogen-containing compounds that can be degraded to produce volatile nitrogen compounds include those containing amine groups, amide groups, nitrile groups, or any combination thereof. Other types of nitrogen-containing compounds that may be analyzed in this manner include, for example, ureas and carbamates and polymers containing these functional groups. Nitrogen-containing polymers or compounds containing amide groups may include primary, secondary, and/or tertiary amides. Similarly, nitrogen-containing polymers or compounds containing amine groups may include primary, secondary, and/or tertiary amines, as well as quaternized amines. Accordingly, surfactants and like entities containing quaternized amine groups may be analyzed by the methods of the present disclosure.

The type of volatile nitrogen compound distilled from the oilfield retort may vary depending upon the structure of the nitrogen-containing polymer or compound from which it is formed and the type of degradation reaction it undergoes. In some embodiments, the volatile nitrogen compound may comprise ammonia, which can be produced from hydrolysis of primary amides or nitrile groups. However, volatile nitrogen compounds that can be produced and analyzed in the methods of the present disclosure are not limited in this respect. For example, low molecular weight amines such as methylamine, ethylamine, dimethylamine, diethylamine, and the like may be produced by a degradation reaction and undergo further analysis. Such volatile nitrogen compounds may be produced upon hydrolysis of secondary amides or tertiary amides, for example. Low molecular weight amines, as well as ammonia, can also be produced by thermally or oxidatively induced degradation processes as well.

In some embodiments, the treatment fluids containing the nitrogen-containing polymer or nitrogen-containing compound may comprise an aqueous carrier fluid. Aqueous carrier fluids may be obtained from any suitable source. Suitable aqueous carrier fluids may include, for example, fresh water, acidified water, treated water, salt water, seawater, brackish water, produced water, flowback water, brine (e.g., a saturated salt solution), or an aqueous salt solution (e.g., a non-saturated salt solution). Suitable aqueous carrier fluids may comprise either a known amount of nitrogen-containing compounds, or, more desirably, the aqueous carrier fluid may be substantially free of nitrogen-containing compounds. By having an aqueous carrier fluid that is substantially free of nitrogen-containing compounds, a background of volatile nitrogen compounds may be lessened when practicing the methods of the present disclosure.

In some embodiments, an organic co-solvent may be present in combination with an aqueous carrier fluid in the treatment fluid. Suitable organic co-solvents may include, but are not limited to, glycols and alcohol solvents, for example. When present, an amount of the organic co-solvent may range between about 1% to about 50% by volume of the treatment fluid. In addition to promoting solubility of the nitrogen-containing polymer or nitrogen-containing compound in the treatment fluid, the presence of the organic co-solvent in the oilfield retort may also better promote degradation to form volatile nitrogen compounds, such as through a hydrolysis reaction.

In alternative embodiments, an organic co-solvent, such as methanol, ethanol, or propanol, for example, may be added to the oilfield retort in combination with the sample of the treatment fluid and the aqueous base. As noted above, the presence of the organic co-solvent may facilitate hydrolysis to form volatile nitrogen compounds in the methods of the present disclosure.

Non-aqueous carrier fluids may also be present in the treatment fluids, and such treatment fluids may too be analyzed successfully using the methods of the present disclosure. Suitable non-aqueous carrier fluids include, for example, an alkane or cycloalkane, an olefin, an aromatic hydrocarbon, a paraffin, diesel, mineral oil, plant oils, kerosene or desulfurized kerosene, or any combination thereof.

In some embodiments, the treatment fluid can be in emulsified form. The emulsified form may comprise an oil-in-water emulsion or a water-in-oil emulsion. The continuous phases of these types of emulsions may comprise the aqueous or non-aqueous carrier fluids, respectively, mentioned previously. Similarly, in still other embodiments, the treatment fluid may be foamed.

In more particular embodiments of the present disclosure, the treatment fluid may comprise an aqueous carrier fluid and a nitrogen-containing polymer. In such embodiments, the nitrogen-containing polymer may be soluble or insoluble in the aqueous carrier fluid, and the nitrogen-containing polymer is not considered to be particularly limited in structure, provided that it can be effectively degraded to form one or more volatile nitrogen compounds. As noted above, the methods of the present disclosure may be effectively used to analyze for both soluble and insoluble nitrogen-containing polymers and compounds.

In some embodiments, the treatment fluid may comprise an aqueous carrier fluid and the nitrogen-containing polymer may be soluble in the aqueous carrier fluid. Acrylamide polymers and copolymers, any derivative thereof or any combination thereof represent illustrative examples of nitrogen-containing polymers that can be soluble in aqueous carrier fluids. More specific examples of aqueous-soluble acrylamide polymers and copolymers include, for example, poly(meth)acrylamide, poly(N,N-dimethylacrylamide), poly(N,N-dimethylmethacrylamide), partially hydrolyzed poly(meth)acrylamide, copolymers of (meth)acrylamide and t-butyl acrylate, copolymers of (meth)acrylamide and 2-acrylamido-2-methyl propane sulfonate, and the like. Other aqueous-soluble nitrogen-containing polymers may be analyzed similarly.

In some embodiments, the treatment fluid may comprise an aqueous carrier fluid and the nitrogen-containing polymer may be insoluble in the aqueous carrier fluid. When present in insoluble form in the aqueous carrier fluid, the nitrogen-containing polymer may be present in the treatment fluid in various non-limiting forms such as emulsified, suspended, solubilized, and the like. Any of these insoluble polymer forms may be suitably analyzed by the methods of the present disclosure.

In more particular embodiments, illustrative aqueous-insoluble, nitrogen-containing polymers that may be analyzed by the methods of the present disclosure include, for example, acrylonitrile polymers or copolymers, any derivative thereof, or any combination thereof. Other aqueous-insoluble, nitrogen-containing polymers may include, for example, polyamides and polyurethanes.

In addition to nitrogen-containing polymers and nitrogen-containing compounds, treatment fluids that may be analyzed by the methods of the present disclosure can also contain a variety of other components. Additional treatment fluid components that may be present include, for example, acids, bases, silica scale control additives, surfactants, gel stabilizers, anti-oxidants, polymer degradation prevention additives, relative permeability modifiers, scale inhibitors, corrosion inhibitors, foaming agents, defoaming agents, antifoaming agents, emulsifying agents, de-emulsifying agents, iron control agents, proppants or other particulates, particulate diverters, salts, fluid loss control additives, gas, catalysts, clay control agents, dispersants, flocculants, scavengers (e.g., $H_2S$ scavengers, $CO_2$ scavengers or $O_2$ scavengers), gelling agents, lubricants, breakers, friction reducers, bridging agents, viscosifiers, weighting agents, solubilizers, pH control agents (e.g., buffers), hydrate inhibitors, consolidating agents, bactericides, catalysts, clay stabilizers, breakers, delayed release breakers, and the like. The additional treatment fluid components may be nitrogen-free, or if not nitrogen-free, the quantity of volatile nitrogen compounds resulting from the additional treatment fluid components may be accounted for as background when determining the quantity of the nitrogen-containing compound or nitrogen-containing polymer. Other considerations to be made in choosing additional treatment fluid components that may be present include selecting substances that do not interfere with the distillation of volatile nitrogen compounds from the oilfield retort. For example, additional treatment fluid components that decompose under the distillation conditions (e.g., by forming tar or char) and trap volatile nitrogen compounds within the oilfield retort may be unsuitable for inclusion within the treatment fluid during analysis.

The aqueous base that is placed in the oilfield retort in combination with the treatment fluid is not considered to be particularly limited, provided that the aqueous base is effective for promoting hydrolysis of the nitrogen-containing polymer or nitrogen-containing compound to form one or more volatile nitrogen compounds. In specific embodiments, the aqueous base can be substantially nitrogen-free, so as not to contribute to a background nitrogen analysis. Suitable aqueous bases for use in the methods of the present disclosure may include, for example, alkali metal bases and alkaline earth metal bases. In this regard, suitable aqueous bases may include, but are not limited to, lithium hydroxide, sodium hydroxide, potassium hydroxide, calcium hydroxide, magnesium hydroxide, barium hydroxide, and the like.

Similarly, the concentration of the aqueous base may be chosen such that it is effective for promoting hydrolysis of the nitrogen-containing compound or nitrogen-containing polymer under the conditions present in the oilfield retort. Suitable concentrations of the aqueous base may range between about 1 M and about 10 M, or between about 1 M and about 6 M, or between about 4 M and about 10 M, or between about 3 M and about 7 M.

The temperature at which the oilfield retort is operated may be selected to effectively promote degradation of the nitrogen-containing polymer or compound and ensuing distillation of volatile nitrogen compounds therefrom. In various embodiments, the sample of the treatment fluid and the aqueous base may be heated in the oilfield retort at a temperature ranging between about 500° F. and about 700° F. In more particular embodiments, the temperature may range between about 550° F. and about 650° F., or between about 575° F. and about 625° F. In a particular embodiment, the sample of the treatment fluid and the aqueous base may be heated at a temperature of about 600° F.

As noted above, the volatile nitrogen compounds distilled from the oilfield retort generally comprise basic nitrogen compounds such as ammonia and low molecular weight amines. In order to effectively collect or trap the distilled volatile nitrogen compounds for further analysis, the volatile nitrogen compounds may be distilled into a receiving solution comprising an acid. The acid in the receiving solution at least partially protonates the volatile nitrogen compounds and converts them into a substantially non-volatile salt form, thereby trapping the volatile nitrogen compounds in the receiving solution. In addition to the acid, the receiving solution comprises water in which the acid is dissolved.

In some embodiments, the acid in the receiving solution may comprise boric acid. In the case where the volatile nitrogen compound comprises ammonia and the acid in the receiving solution comprises boric acid, a nonvolatile 1:1 ammonium borate complex may be produced in the receiving solution. At low concentrations, aqueous solutions of the ammonium borate complex may have a pH above about 8, which may be beneficial for further analysis, as discussed below. As an alternative to boric acid, other acids such as hydrochloric acid, hydrobromic acid, acetic acid, formic acid, or the like may be present in the receiving solution in order to trap the volatile nitrogen compounds therein. One or more of these acids may optionally be used in combination with boric acid, if desired. Use of strong acids in the receiving solution may influence how analysis of the receiving solution is conducted, as discussed hereinafter.

The amount of acid in the receiving solution may be selected to be sufficient to protonate at least a portion of the volatile nitrogen compounds distilled into the receiving solution. In some embodiments, the amount of acid in the receiving solution may be sufficient to react with all of the volatile nitrogen compounds distilled from the oilfield retort, thereby lessening the likelihood of loss to the surrounding environment and resulting in inaccurate analyses. That is, in some embodiments, at least one stoichiometric equivalent of the acid may be present in the receiving solution. In other various embodiments, less than a stoichiometric equivalent of the acid may be present in the receiving solution, with only a portion of the volatile nitrogen compounds being trapped as a salt, and the remaining volatile nitrogen compounds simply being solubilized by the receiving solution.

As discussed further below, analysis of the receiving solution may take place through titration. In the case of strong acids, such as hydrochloric acid or sulfuric acid being present in the receiving solution, it can be desirable for only a small stoichiometric excess of acid to be present in the receiving solution. Otherwise, large amounts of base may be required to neutralize the excess acid during titration. In the case of boric acid being present in the receiving solution, however, an unmeasured excess of this acid may be present, since titration may be based upon neutralization of a borate complex of the volatile nitrogen compound. With boric acid, titration of the borate complex may take place with a standardized solution of an acid titrant, such as sulfuric acid.

Once distillation of volatile nitrogen compounds from the oilfield retort to the receiving solution is complete or substantially complete, the quantity of distilled volatile nitrogen compounds may then be determined. In more particular embodiments, determining the quantity of volatile nitrogen compounds distilled from the oilfield retort may take place by titrating at least a portion of the receiving solution. Titration of the receiving solution may be conducted manually or using automated equipment at the discretion of an operator. Titration may further take place using a suitable indicator and a suitable acid titrant or base titrant. Suitable acid titrants for borate complexes of volatile nitrogen compounds may include strong acids such as sulfuric acid or hydrochloric acid, for example. Suitable indicators for borate complexes of volatile nitrogen compounds may provide a color change at or near the equivalence point of the receiving solution. Illustrative indicators for titrating borate complexes of volatile nitrogen compounds include, for example, a mixed indicator of bromocresol green and methyl red, a mixed indicator solution of methylene blue and methyl red, and methyl orange.

Accordingly, in more specific embodiments, methods described herein may comprise: placing a sample of a treatment fluid and an aqueous base in an oilfield retort, the treatment fluid comprising a nitrogen-containing polymer; heating the sample of the treatment fluid and the aqueous base together in the oilfield retort until at least the nitrogen-containing polymer has been substantially degraded to one or more volatile nitrogen compounds; distilling the one or more volatile nitrogen compounds from the oilfield retort and collecting the one or more volatile nitrogen compounds in a receiving solution comprising an acid; titrating at least a portion of the receiving solution with an acid titrant; and correlating an amount of the acid titrant used to titrate the receiving solution with a quantity of the nitrogen-containing polymer present in the sample of the treatment fluid.

Figure 2:
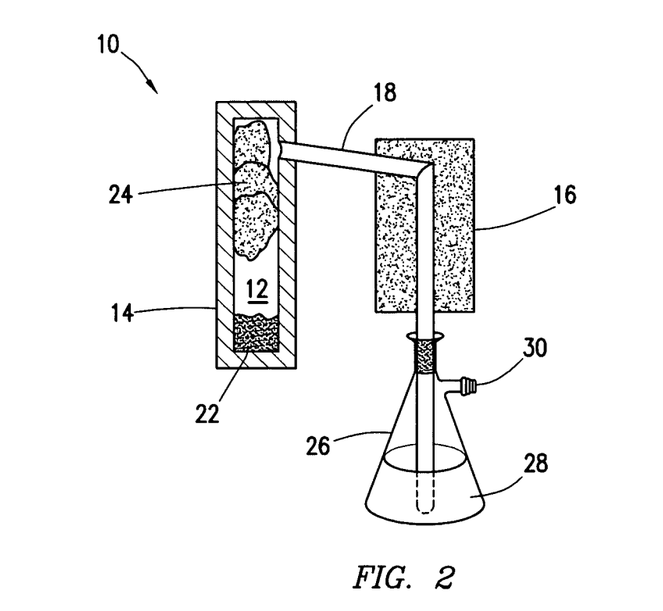
FIG. 2 shows an illustrative schematic of an oilfield retort whose output is coupled to a receiving solution.

The methods of the present disclosure will now be described in more detail with reference to FIG. 2. FIG. 2 shares several elements in common with FIG. 1 and will be better understood with reference thereto. Like reference characters will be used to denote common elements having similar structures and functions, and the common elements not be described again in detail in the interest of brevity.

FIG. 2 shows an illustrative schematic of an oilfield retort whose output is coupled to a receiving solution. As shown in FIG. 2, oilfield retort 10 contains heating jacket 14 substantially surrounding retort cell 12. Within retort cell 12 is placed mixture 22 comprising an aqueous base and a treatment fluid comprising a nitrogen-containing polymer or other nitrogen-containing compound. At least a portion of the headspace above mixture 22 is optionally packed with non-reactive, porous material 24, such as steel wool or glass wool, for example.

Mixture 22 is then heated using heating jacket 14 at a temperature and for a time sufficient to promote hydrolysis or a like degradation reaction of the nitrogen-containing polymer into one or more volatile nitrogen compounds. Optionally, the temperature and the rate of heating may be adjusted with a controller (not shown). The heated mixture may reflux within retort cell 12, aided in this respect by non-reactive, porous material 24, in order to promote complete or near-complete conversion of the nitrogen-containing polymer into volatile nitrogen compounds. The volatile nitrogen compounds travel from retort cell 12 to condensation column 16 via line 18, where they cool down from the reflux temperature. Other components of the treatment fluid or the aqueous base (e.g., water or other solvents) may co-distill with the volatile nitrogen compounds, but as long as they do not interfere with subsequent analyses of the distilled volatile nitrogen compounds, they may be present in the distillate.

After being cooled down from the reflux temperature, the volatile nitrogen compounds and any co-distilled components are passed into receiving vessel 26 containing receiving solution 28. The volatile nitrogen compounds may be introduced to receiving solution 28 in gaseous form, or they may be dispersed as a fluid phase along with co-distilled liquid components from mixture 22. The output of condensation column 16 may introduced directly (i.e., bubbled) into receiving solution 28 so that the volatile nitrogen compounds become trapped therein and do not have an opportunity to escape through gas outlet 30. Line 18 may extend directly from the outlet of condensation column 16 into receiving solution 28, as depicted in FIG. 2, or an extension tube, such as rubber tubing or another appropriate type of conduit, may extend line 18 into receiving solution 28. In either case, the output of condensation column 18 is bubbled into receiving solution 28. Although gas outlet 30 has been depicted as a sidearm of receiving vessel 26 in FIG. 2, it is to be recognized that any structure capable of venting receiving vessel 26 and preventing pressure buildup of a closed system may be employed.

Once liquid and gas evolution from condensation column 16 has visibly ceased, receiving vessel 26 may be removed, and at least a portion of receiving solution 28 may undergo further analysis in order to determine the amount of volatile nitrogen compounds present therein. In some embodiments, receiving solution 28 may be titrated to its equivalence point, as discussed above. In some embodiments, the entirety of receiving solution 28 may be titrated, in which case titration may take place directly in receiving vessel 26. In other various embodiments, a measured aliquot of receiving solution 28 may be withdrawn and titrated through an appropriate titration technique using a standardized titrant having a known concentration.

Upon completion of the titration, the number of moles of volatile nitrogen compounds present in the receiving solution may then be calculated based upon the standardized concentration of the titrant. This value may then be correlated to the amount of nitrogen-containing polymer or other nitrogen-containing compound that is present in mixture 22. For example, if the structure of a nitrogen-containing polymer or a nitrogen-containing compound is known, one may determine the amount present in mixture 22 by taking into account stoichiometry and the amount of volatile nitrogen compounds present in receiving solution 28.

In other various embodiments, determining the quantity of nitrogen-containing polymer in the treatment fluid may be based upon a calibration curve or lookup table containing data for treatment fluids with known quantities of the nitrogen-containing polymer. In this regard, a plurality of samples containing known amounts of the nitrogen-containing polymer may be analyzed as described above, and the titration data may then be tabulated or plotted as a function of the known amount of nitrogen-containing polymer. Thereafter, a sample containing an unknown amount of nitrogen-containing polymer may be analyzed, and the titration data for the unknown sample may then be compared to the results of the known samples in order to determine the amount of nitrogen-containing polymer present.

Embodiments Disclosed Herein Include:

A. Methods for assaying nitrogen-containing compounds. The methods comprise: receiving a sample of a treatment fluid comprising a nitrogen-containing compound; placing the sample of the treatment fluid and an aqueous base in an oilfield retort; heating the sample of the treatment fluid and the aqueous base together in the oilfield retort at least until the nitrogen-containing compound has been substantially degraded to one or more volatile nitrogen compounds; distilling the one or more volatile nitrogen compounds from the oilfield retort; and determining a quantity of the nitrogen-containing compound in the sample of the treatment fluid based upon a quantity of the one or more volatile nitrogen compounds distilled from the oilfield retort.

B. Methods for assaying nitrogen-containing compounds. The methods comprise: placing a sample of a treatment fluid and an aqueous base in an oilfield retort, the treatment fluid comprising a nitrogen-containing polymer; heating the sample of the treatment fluid and the aqueous base together in the oilfield retort at least until the nitrogen-containing polymer has been substantially degraded to one or more volatile nitrogen compounds; distilling the one or more volatile nitrogen compounds from the oilfield retort and collecting the one or more volatile nitrogen compounds in a receiving solution comprising an acid; titrating at least a portion of the receiving solution with an acid titrant; and correlating an amount of the acid titrant used to titrate the receiving solution with a quantity of the nitrogen-containing polymer present in the sample of the treatment fluid.

Each of Embodiments A and B May have One or More of the Following Additional Elements in any Combination:

Element 1: wherein the nitrogen-containing compound comprises a nitrogen-containing polymer.

Element 2: wherein the nitrogen-containing polymer comprises an amine group, an amide group, a nitrile group, a urea group, a carbamate group, or any combination thereof.

Element 3: wherein the treatment fluid comprises an aqueous carrier fluid and the nitrogen-containing polymer is soluble in the aqueous carrier fluid.

Element 4: wherein the nitrogen-containing polymer comprises an acrylamide polymer or copolymer, any derivative thereof, or any combination thereof.

Element 5: wherein the treatment fluid comprises an aqueous carrier fluid and the nitrogen-containing polymer is insoluble in the aqueous carrier fluid.

Element 6: wherein the nitrogen-containing polymer comprises an acrylonitrile polymer or copolymer, any derivative thereof, or any combination thereof.

Element 7: wherein the one or more volatile nitrogen compounds are distilled into a receiving solution comprising an acid.

Element 8: wherein the method further comprises: determining the quantity of the one or more volatile nitrogen compounds distilled from the oilfield retort by titrating at least a portion of the receiving solution.

Element 9: wherein the acid in the receiving solution comprises boric acid.

Element 10: wherein the one or more volatile nitrogen compounds comprises ammonia.

Element 11: wherein the sample of the treatment fluid and the aqueous base are heated at a temperature ranging between about 500° F. and about 700° F.

Element 12: wherein the sample of the treatment fluid is substantially degraded by a hydrolysis reaction.

By Way of Non-Limiting Example, Exemplary Combinations Applicable to A and B Include:

The method of A in combination with elements 1 and 3.
The method of A in combination with elements 1 and 5.
The method of A in combination with elements 7 and 8.
The method of A in combination with elements 8 and 9.
The method of A in combination with elements 11 and 12.
The method of A in combination with elements 1 and 12.
The method of A in combination with elements 7, 9 and 10.
The method of B in combination with elements 2 and 3.
The method of B in combination with elements 2 and 5.
The method of B in combination with elements 3 and 4.
The method of B in combination with elements 5 and 6.
The method of B in combination with elements 9 and 10.
The method of B in combination with elements 10 and 11.
The method of B in combination with elements 10 and 12.
The method of B in combination with elements 11 and 12.

To facilitate a better understanding of the present disclosure, the following examples of preferred or representative embodiments are given. In no way should the following examples be read to limit, or to define, the scope of the disclosure.

EXAMPLES

Example 1: Quantification of Acrylonitrile-Butadiene Copolymer in a Water-Based Drilling Fluid Drilling fluids formulated from the following components were prepared: water, xanthan, starch, calcium carbonate, REV DUST (simulated drill cuttings, containing calcium montmorillonite clay, Milwhite, Inc., Houston, Tex.) and acrylonitrile-butadiene copolymer. 10 mL of the formulated drilling fluid and 5 mL of 5 M sodium hydroxide were then placed in a retort cell. The headspace within the retort cell was packed with steel wool, and the retort cell was then closed and heated to 600° F. Volatile material distilled from the retort cell was collected in 30 mL of a receiving solution containing 1.6% (v/v) boric acid. Heating was continued until no further liquid or gas was observed to be exiting the condensation column of the retort apparatus. At this point, the receiving solution was then titrated with 0.005 N sulfuric acid to a bromocresol green-methyl red endpoint (pH~5). The volume of acidic titrant was then plotted against the known polymer concentration for drilling fluids having several different polymer loadings.

Figure 3:
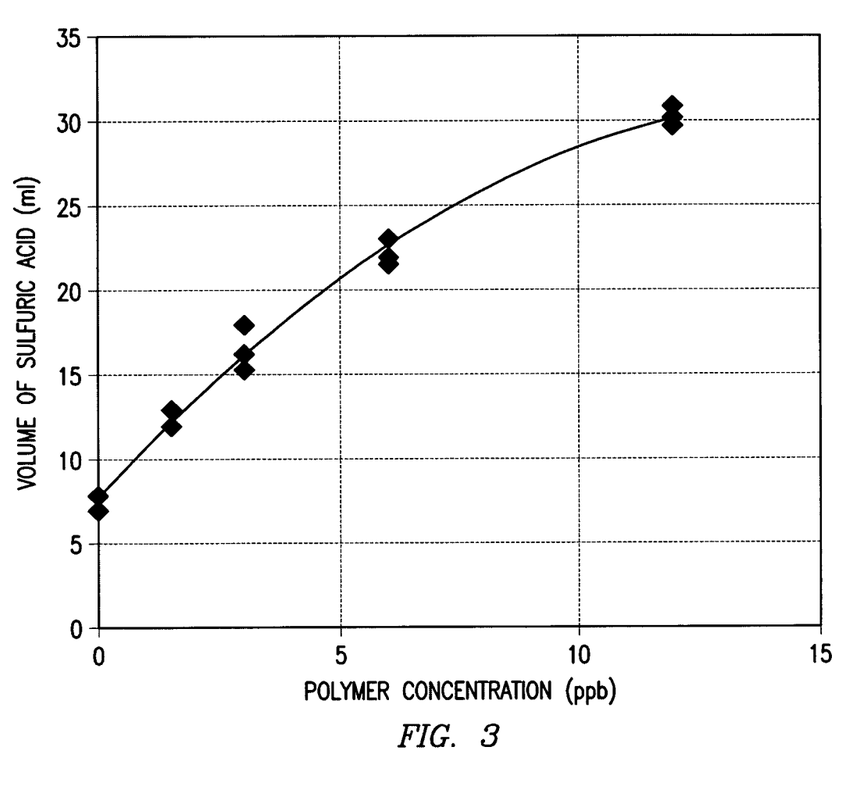
FIG. 3 shows an illustrative plot of acid titrant volume against acrylonitrile-butadiene polymer concentration.

FIG. 3 shows an illustrative plot of acidic titrant volume against acrylonitrile-butadiene polymer concentration. As shown in FIG. 3, there was good reproducibility between replicate samples at the same polymer concentration, even though there was an element of non-linearity to the plot at the higher polymer loadings. Moreover, the non-zero y-axis intercept at zero polymer loading is believed to be due to the presence of background nitrogen compounds that become trapped in the receiving solution.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method comprising:
    receiving a sample of a treatment fluid comprising a nitrogen-containing compound;
    placing the sample of the treatment fluid and an aqueous base in an oilfield retort, the oilfield retort comprising a heating jacket that surrounds the oilfield retort, wherein at least a portion of a headspace above the sample of the treatment fluid and the aqueous base is packed with steel wool or glass wool;
    heating, with the heating jacket, the sample of the treatment fluid and the aqueous base together in the oilfield retort at least until the nitrogen-containing compound has been substantially degraded to one or more volatile nitrogen compounds;
    distilling the one or more volatile nitrogen compounds from the oilfield retort; and
    determining a quantity of the nitrogen-containing compound in the sample of the treatment fluid based upon a quantity of the one or more volatile nitrogen compounds distilled from the oilfield retort.

2. The method of claim 1, wherein the nitrogen-containing compound comprises a nitrogen-containing polymer.

3. The method of claim 2, wherein the nitrogen-containing polymer comprises an amine group, an amide group, a nitrile group, a urea group, a carbamate group, or any combination thereof.

4. The method of claim 2, wherein the treatment fluid comprises an aqueous carrier fluid and the nitrogen-containing polymer is soluble in the aqueous carrier fluid.

5. The method of claim 4, wherein the nitrogen-containing polymer comprises an acrylamide polymer or copolymer, any derivative thereof, or any combination thereof.

6. The method of claim 2, wherein the treatment fluid comprises an aqueous carrier fluid and the nitrogen-containing polymer is insoluble in the aqueous carrier fluid.

7. The method of claim 6, wherein the nitrogen-containing polymer comprises an acrylonitrile polymer or copolymer, any derivative thereof, or any combination thereof.

8. The method of claim 1, wherein the one or more volatile nitrogen compounds are distilled into a receiving solution comprising an acid.

9. The method of claim 8, further comprising:
    determining the quantity of the one or more volatile nitrogen compounds distilled from the oilfield retort by titrating at least a portion of the receiving solution.

10. The method of claim 8, wherein the acid in the receiving solution comprises boric acid.

11. The method of claim 1, wherein the one or more volatile nitrogen compounds comprises ammonia.

12. The method of claim 1, wherein the sample of the treatment fluid and the aqueous base are heated at a temperature ranging between about 500° F. and about 700° F.

13. The method of claim 1, wherein the sample of the treatment fluid is substantially degraded by a hydrolysis reaction.

* * * * *